(12) United States Patent
Saitoh

(10) Patent No.: US 7,452,505 B2
(45) Date of Patent: Nov. 18, 2008

(54) METHOD FOR ANALYZING BLOOD TEST SAMPLE AND DRY ANALYTICAL ELEMENT AND ANALYTICAL KIT UTILIZING THE METHOD

(75) Inventor: Hitomi Saitoh, Saitama (JP)

(73) Assignee: Fujifilm Corporation, Tokyo (JP)

( * ) Notice: Subject to any disclaimer, the term of this patent is extended or adjusted under 35 U.S.C. 154(b) by 400 days.

(21) Appl. No.: 10/422,087

(22) Filed: Apr. 24, 2003

(65) Prior Publication Data

US 2003/0202904 A1 Oct. 30, 2003

(30) Foreign Application Priority Data

Apr. 25, 2002 (JP) .............................. 2002-123334

(51) Int. Cl.
*G01N 21/00* (2006.01)
*G01N 21/77* (2006.01)
*G01N 33/543* (2006.01)
*C12Q 1/32* (2006.01)

(52) U.S. Cl. ............................ 422/56; 422/58; 435/26; 436/169; 436/518

(58) Field of Classification Search .................... 422/56, 422/58; 435/26; 436/169, 518
See application file for complete search history.

(56) References Cited

U.S. PATENT DOCUMENTS

| | | | | | |
|---|---|---|---|---|---|
| 3,853,721 | A | * | 12/1974 | Darlington et al. ........... | 205/519 |
| 3,992,347 | A | * | 11/1976 | Vary ........................... | 524/269 |
| 4,267,234 | A | * | 5/1981 | Rembaum .................... | 428/403 |
| 4,337,222 | A | * | 6/1982 | Kitajima et al. ............... | 422/56 |
| 4,781,890 | A | * | 11/1988 | Arai et al. ...................... | 422/56 |
| 4,803,159 | A | * | 2/1989 | Smith-Lewis ................ | 435/26 |
| 4,981,805 | A | * | 1/1991 | Yazawa et al. ............... | 436/169 |
| 6,093,559 | A | * | 7/2000 | Bookbinder et al. ......... | 435/183 |
| 2002/0160212 | A1 | * | 10/2002 | Yamashita et al. ........... | 428/458 |

* cited by examiner

*Primary Examiner*—Jill Warden
*Assistant Examiner*—Lore Ramillano
(74) *Attorney, Agent, or Firm*—Birch, Stewart, Kolasch & Birch, LLP

(57) ABSTRACT

Objects of the present invention are to provide a method for analyzing a blood test sample containing blood platelet collected from a human body to detect presence of an analyte in the test sample, wherein fluctuations of measured results due to difference of processing mode of the test sample is eliminated, a dry analytical element and an analytical kit utilizing the method. The objects are achieved by a blood analytical method in which surfactant added to the blood test sample is at least one selected from surfactants that do not destroy blood platelet, a dry analytical element and an analytical kit utilizing the method.

1 Claim, 1 Drawing Sheet

Constitution of dry analytical element for LDH

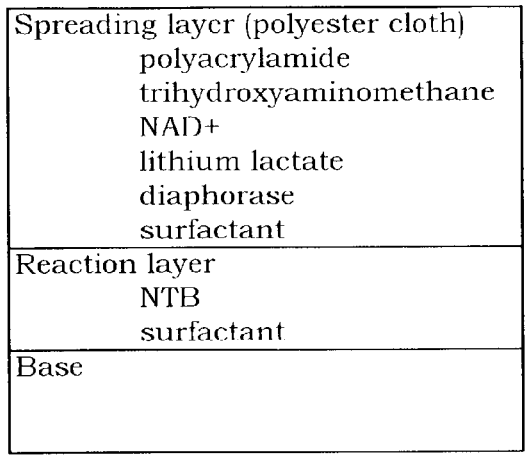

← spreading layer containing substrate

← reaction layer containing color indicator

← support

Fig. 1 Constitution of dry analytical element for LDH

| Spreading layer (polyester cloth) |
| --- |
| polyacrylamide<br>trihydroxyaminomethane<br>NAD+<br>lithium lactate<br>diaphorase<br>surfactant |
| Reaction layer<br>NTB<br>surfactant |
| Base |

← spreading layer containing substrate

← reaction layer containing color indicator

← support

METHOD FOR ANALYZING BLOOD TEST SAMPLE AND DRY ANALYTICAL ELEMENT AND ANALYTICAL KIT UTILIZING THE METHOD

FIELD OF THE INVENTION

This invention relates to a method for analyzing a blood test sample containing blood platelet collected from a human body, a dry analytical element and an analytical kit utilizing the method.

BACKGROUND OF THE INVENTION

An analytical method, in which blood collected from a human body is analyzed as a test sample to diagnose human diseases, has conventionally been performed. The method is generally classified into two types, that is, a wet analytical method in which a reagent(s) necessary for designed analysis and a test sample are added into water to prepare a solution to allow some detectable reaction to take place; and a dry analytical method in which a test sample is supplied onto a layer (gelatin layer, for example) containing reagents previously in dry state to allow some detectable reaction to take place in the layer.

In the case where enzyme activity is measured by utilizing a dry analytical method, for example, such an analytical element is utilized that has one or more layers containing reagents in dry state on an undercoated transparent polyethylene terephthalate (PET) base and a spreading layer of tricot knitted cloth made of polyester spun yarn laminated on the layer.

The spreading layer plays an important roll to make a supplied test sample diffuse uniformly in lateral and longitudinal directions. In other word, uniform contact between a reagent and the test sample, which is achieved by stirring of a solution in the wet analytical method above described, is realized by the uniform diffusion of the test sample in the spreading layer.

Such dry analytical elements include a dry analytical element suitable for analyzing activity of lactate dehydrogenase (LDH) in a test sample. The analytical element contains lactic acid or salts thereof and nicotine amide coenzyme in an oxidized form (NAD$^+$). By utilizing the analytical element, nicotine amide coenzyme in a reduced form (NADH) produced through reaction is detected with a coloring reagent and so on.

However, in the case of quantitative analysis of LDH in a test sample by utilizing such a dry analytical element, measured values sometimes fluctuate (shift to a higher value) depending on processing method of the test sample and some countermeasures for improvement have been desired.

On the other hand, in a wet analytical method, reaction is allowed to occur by mixing an aqueous solution dissolving a reagent(s) necessary for designed analysis and a blood test sample. In the wet analytical method also, measured results sometimes fluctuate depending on processing method of the test sample and some countermeasures for improvement have been desired.

SUMMARY OF THE INVENTION

An object of the present invention is to provide a method for analyzing a blood test sample containing blood platelet, which is collected from a human body, to detect an analyte in the test sample, the method being free from fluctuations of measured results irrespective of difference in processing method of the test sample.

Another object of the present invention is to provide a dry analytical element utilizing the method.

Another object of the present invention is to provide a kit for analyzing a blood test sample utilizing the method.

As a result of intensive studies, the present inventors found that blood platelet remains in a plasma test sample in the case where centrifugal operation for obtaining a plasma test sample from whole blood is insufficient, and that the blood platelet remaining in the plasma sample is destroyed by surfactant existing in the dry analytical element or in a reagent solution, resulting in fluctuations of measured values. Accordingly, above-described objects are achieved by a method for analyzing blood sample by mixing the blood sample with at least one surfactant selected from surfactants that do not destroy substantially blood platelet in the blood sample, and a dry analytical element and an analytical kit utilizing the method.

BRIEF DESCRIPTION OF THE DRAWING

FIG. 1 is a conceptual diagram of a dry analytical element for measuring LDH, which is one of dry analytical elements according to the invention.

DETAILED DESCRIPTION OF THE INVENTION

Hereinafter, each of the dry analytical method and the wet analytical method according to the present invention will be described separately.

(1) The Dry Analytical Method

The analytical method according to the present invention can be adapted to a dry analytical element for detecting LDH, GOT, ACP or the like in a test sample. Herein, an analytical element for analyzing LDH will be described as an example for convenience.

The basic constitution of the dry analytical element for analyzing quantitatively LDH in a test sample is disclosed in, for example, Japanese Patent No. H5 (1993)-060360, but is not limited to the same. For example, such an analytical element may be also useful that is constituted of a light permeable water impermeable plastic base (PET base, for example) having an undercoating layer, a water penetrative layer containing a coloring agent disposed on the base, and a spreading layer, which is disposed on the water penetrative layer, containing a surfactant that is a characteristic of the present invention, a lactate, an electron transmitter and NAD$^+$.

As an example, constitution of layers and reagents contained therein are illustrated in FIG. 1. Here, "NTB" means 3,3'-(3,3'-dimethoxy-4,4'-biphenylene)bis[2-(p-nitrophenyl)-5-phenyltetrazoliumchloride].

As for a surfactant used in the dry analytical element according to the invention, at least one surfactant selected from surfactants that substantially do not break blood platelet is preferable. Here, the phrase "a surfactant that substantially does not break blood platelet" means "a surfactant that results in measured values of LDH (generally, of an analyte) with a tolerable plus error when it is added into the spreading layer by an amount that realizes uniform spreading of a test sample in the spreading layer". Any surfactant may not break blood platelet if an added amount thereof is not too much. However, if it does not realize uniform spreading of a test sample in the spreading layer, a dry analytical element according to the invention will never be accomplished.

It is evident from results of examples and reference examples shown later that whether a surfactant used in the blood analysis method breaks blood platelet or not is closely related to the result of the blood analysis.

As for such the surfactant, at least one selected from silicon series or fluorocarbon series surfactants is preferable and, at least one selected from silicon series surfactant is more preferable.

Among silicon series surfactants, those selected from modified polyether silicon series surfactants represented by following general formulae (1) to (4) are preferable:

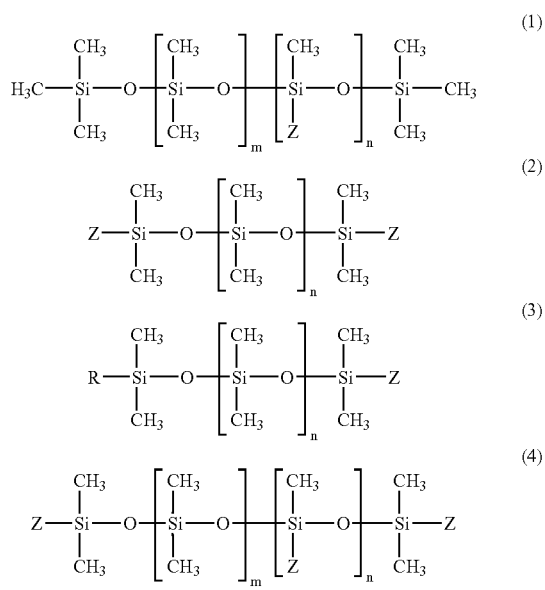

in which Z represents an organic group represented by the general formula $-R-(C_2H_4O)_a-(C_3H_6O)_bR$.

Specific examples thereof include modified silicone oil KF351, KF352, KF353, KF354L and the like, manufactured by Shinnetu Chemical Industry Inc. Among them, KF353 is preferable.

Fluorocarbon series surfactants selected from a compound are preferably represented by the following formula:

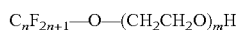

$C_nF_{2n+1}-O-(CH_2CH_2O)_mH$ in which m represents an integer of 5 to 7, and n represents an integer of 6 to 14 independently from each other.

Specific examples of fluorocarbon series surfactant represented by the above formula include POE(10)perfluoroalkyl (trade name F142D; manufactured by DAINIPPON INK AND CHEMICALS, INC.) and POE(6)perfluoroalkyl ethoxylate (trade name F1405; manufactured by DAINIPPON INK AND CHEMICALS, INC.).

Amount of the surfactant to be added ranges 0.1-2 g/m², preferably 0.3-1.2 g/m², and two kinds of surfactants described above may be used by mixing at any ratio.

GOT, ACP and the like, in addition to LDH, can be listed as analytes to be an object of the analysis by using the dry analytical element according to the invention, since these analytes in a test sample also increase by breakdown of blood platelet. Dry analytical elements for analyzing these analytes are disclosed in, for example, Japanese Patent No. H4 (1992)- 000640, Japanese Patent Laid-open Publication No. S63 (1988)-088000, and so on.

(2) The Wet Analytical Method

Next, description will be made on the case where the blood analytical method according to the invention is applied to the wet analytical method.

In the wet analytical method, reagents necessary for analysis are supplied as an aqueous solution. In the aqueous solution, a surfactant is added for the purpose of, for example, pipetting smoothly a small amount of the aqueous solution. Depending on kind of the surfactant, measured values may be not accurate (deviate to a higher value) due to the reason described above in the case of the dry analytical method.

Surfactants usable in the wet analytical method also can be selected from those described above. Here, since uniform spreading of a blood test sample in the spreading layer, which is indispensable for the dry analytical method, is not required for the wet analytical method, more surfactants can be selected for use in the wet analytical method.

The present invention will be described further in detail, however the invention is not limited thereto.

EXAMPLES

Example 1

(1) Preparation of a Dry Analytical Slide for Quantitatively Analyzing LDH

A reaction layer having thickness of 40 μm was provided by coating and drying an aqueous solution containing following components on a PET film of 180 μm in thickness, which is flat, colorless, transparent and undercoated with gelatin:

| | |
|---|---|
| gelatin | 20.0 g/m² |
| NTB | 0.8 g/m² |
| surfactant | 0.8 g/m² |

(adjusted to pH=6 with a dilute NaOH solution) in which polyoxy(2-hydroxy)propylene nonylphenylether (Surfactant 10G; made by Olin Inc.) was used as the surfactant and NTB means 3,3'-(3,3'-dimethoxy-4,4'-biphenylene)bis[2-(p-nitrophenyl)-5-phenyltetrazoliumchloride].

Then, water was supplied on the whole surface of the above-described film in the amount of about 30 g/m² to wet the surface. On the wet surface, a tricot knitted cloth formed by knitting 50 denier PET spun yarn with 36 gauge was laminated with light pressure, then an aqueous solution containing following constituents was coated and dried to prepare a dry analytical element for quantitative analysis of LDH according to the invention.

| | |
|---|---|
| purified water | 100.0 g/m² |
| polyacrylamide | 2.0 g/m² |
| (molecular weight 200000) | |
| lithium lactate | 1.0 g/m² |
| diaphorase | 0.5 KU/m² |
| NAD⁺ | 0.5 g/m² |
| trihydroxy aminomethane | 5.0 g/m² |
| surfactant (1) (HLB = 10) | 0.5 g/m² |
| surfactant (2) (HLB = 16) | 0.5 g/m² |
| (adjusted to pH = 8 with dil. HCl) | |

As for the surfactant (1), KF353 was used, and as for the surfactant (2), KF354 was used (both of them are modified polyether silicon made by Shin-Etsu Chemical Co., Ltd.), which are compounds containing a polyoxyethylene-polyoxypropylenealkyl group as an organic group at a poly siloxane side chain.

The above-described dry analytical element for quantitative analysis of LDH was cut into a chip of 12 mm×13 mm and mounted in a slide holder described in Japanese Patent Laid-open Publication No. S57 (1982)-063452 to prepare a dry analytical slide (1) for quantitative analysis of LDH.

(2) Measurement of LDH Activity

Test samples containing 100000, 200000 and 500000/μL of blood platelet respectively were prepared by adding blood platelet-rich plasma to a standard serum. 10 μL of each of test samples was spotted onto the dry analytical element prepared in above (1). Then, while incubating for 5 min at 37° C., reflection optical density at 540 nm was measured about every 10 seconds with FUJI DRI CHEM 5000 (made by Fuji Photo Film Co., Ltd.). LDH activity was calculated from difference between the reflection density at 1 minute and that at 5 minutes after spotting of the test sample respectively. Results are shown in Table 1.

TABLE 1

Results of measurement of LDH activity

| | LDH activity U/L | | | |
|---|---|---|---|---|
| Blood platelet | Example 1 | Example 2 | Comparative example 1 | Comparative example 2 |
| 100000/μL | 112 | 116 | 125 | 125 |
| 200000/μL | 115 | 119 | 187 | 164 |
| 500000/μL | 114 | 120 | 330 | 238 |

Example 2

A dry analytical slide (4) for quantitative measuring of LDH was prepared in the same manner as Example 1 except that POE (10) perfluoroalkyl ethoxylate (F1405; made by DAINIPPON INK AND CHEMICALS, INC.) was used for the surfactant (1) in the solution to be coated onto the spreading layer. The slide was used for measuring LDH activity by the similar method as Example 1, (2). Results are also shown in Table 1.

Example 3

A film for quantitative measurement of GOT was prepared after the formula described in Japanese Patent H4 (1992)-No. 000640 except that above described KF353 was used in place of Triton X as the surfactant. Similar evaluations same as Example 1 were performed. Results showed that measured values shifted in a higher direction within tolerance for the three test samples.

Example 4

A substrate buffered solution R1 and a coenzyme solution R2 having following constituents respectively were prepared.

| R1: | |
|---|---|
| buffer (diethanolamine) | pH = 9.0 |
| lithium L-lactate | 70 mmol/L |
| surfactant | 0.8% |

(the above-described silicon series surfactant KF353 was used)

| R2: | |
|---|---|
| disodium ethylene diamine tetraacetic acid | 5 mmol/L |
| NAD$^+$ | 30 mmol/L |

First, 3 mL of R1 and 80 μL of each of blood test samples were mixed together, then they were incubated for 5 minutes at 37° C. To each of the mixture, 800 μL of R2 was added at 37° C. to allow reaction to start. At 1 minute and 2 minutes after start of the reaction, absorbance at the wavelength of 340 nm was measured respectively and LDH activity in each test sample was calculated by using a working curve previously drawn up. As for blood test samples, three kinds of samples prepared in the Example 1 (2) were used. Results showed that measured values shifted in a higher direction within tolerance for the three test samples, as was the case with Example 1.

Comparative Example 1

A dry analytical slide (2) for quantitative measurement of LDH was prepared in the same manner as Example 1 except for using polyoxyethylene (10) octylphenylether (HLB=11) for the surfactant (1) and polyoxyethylene (40) octylphenylether (HLB=18) for the surfactant (2) in the solution to be coated on the spreading layer. By using the slide (2), LDH activity in the respective blood test samples was measured in the same method as Example 1 (2). Results are also shown in Table 1.

Comparative Example 2

A dry analytical slide (3) for quantitative measurement of LDH was prepared in the same manner as Example 1 except for using polyoxyethylene (12) oleylether (HLB=11) for the surfactant (1) and polyoxyethylene (40) oleylether (HLB=18) (made by Shin-Etsu Chemical Co., Ltd.) for the surfactant (2) in the solution to be coated on the spreading layer. By using the slide (3), LDH activity in the respective blood test samples was measured in the same method as Example 1 (2). Results are also shown in Table 1.

Comparative Example 3

Dry analytical slides for quantitative measurement of LDH were prepared in the same manner as Example 1 except for using a polyoxyethylene (POE) alkylether series surfactant (EMALEX 505, EMALEX 512 or EMALEX 520; made by Shin-Etsu Chemical Co., Ltd.) for the surfactant (1) and a POE higher alcohol series ether surfactant or an anion surfactant (sodium deoxycholate made by Wako Pure Chemical Industries, Ltd. or NIKKOL OS-14 made by NIKKO CHEMICALS CO., LTD.) for the surfactant (2) respectively in the solution to be coated on the spreading layer. By using these slides, LDH activity in the respective blood test samples was measured in the same method as Example 1 (2) to obtain the results same as those for Comparative example 1.

Comparative Example 4

A substrate buffered solution and a coenzyme solution were prepared in the same manner as Example 4 except for using POE (10) oxtylphenylether in place of KF353, which is the above-mentioned silicon series surfactant. Then, evaluation was performed in the same manner as Example 4. Results represented that significant shift to a higher value was observed in the case of test samples with high concentration of blood platelet as was the case with Comparative example 1.

Reference Example

Degree of destruction of blood platelet was examined for various kinds of surfactants according to the following process. Results are shown in Table 2, in which ○ means no destruction and x means existence of destruction.

(1) Evaluation of Degree of Destruction of Blood Platelet

A surfactant was added to the blood platelet-rich plasma sample to become of 0.8%. Then condition of blood platelet in the sample was observed with an electron microscope. Presence of destruction of blood platelet was determined when the surfactant destroys blood platelet to excrete components in the platelet outside thereof.

(2) Evaluation of LDH Activity

LDH activity of blood platelet-rich plasma samples without surfactant and with 0.6% of surfactant respectively was measured by using an automatic analyzer HITACHI 7170 after the JSCC transferable method (LDHII-HA TESTWAKO; Wako Pure Chemical Industries, Ltd.) at 37° C. In Table 2, "LDH activity" means the activity of the test sample with 0.6% of surfactant, assuming that that of the test sample without surfactant to be 100.

TABLE 2

Degree of destruction of blood platelet by various kinds of surfactants

| Product Name | Chemical Composition | General Formula | Destruction of Blood Platelet | LDH Activity |
|---|---|---|---|---|
| Nissan Nonion | POE (10) octylether | (a) | x | 694 |
| EMALEX 505 | POE (5) oleylether | (b) | x | 295 |
| EMALEX 512 | POE (12) oleylether | (b) | x | 307 |
| EMALEX 520 | POE (20) oleylether | (b) | x | 297 |
|  | POE higher alcohl series ether | (c) | x | 373 |
|  | POE higher alcohl series ether | (c) | x | 703 |
|  | POE higher alcohl series ether | (c) | x | 125 |
| F-142D | POE (10) perfluoroalkyl | (d) | ○ | 104 |
| F-1405 | POE (6) perfluoroalkyl ethoxylate | (d) | ○ | 102 |
| KF351 | polyether modified silicon | (e) | ○ | 101 |
| KF352 | polyether modified silicon | (e) | ○ | 98 |
| KF353 | polyether modified silicon | (e) | ○ | 100 |
| KF354L | polyether modified silicon | (e) | ○ | 102 |
| AM 301 | lauryl dimethylamino acetic acid betaine | (f) | x | 116 |
|  | deoxycholic acid | (g) | x | 199 |
| NIKKOL OS-14 | sodium α-olefin sufonate | (h) | x | 212 |

From the results of the above-described examples, comparative examples and reference example, it can be understood that there is an explicit correlation between the measurement accuracy of LDH activity and degree of destruction of blood platelet by a surfactant. The general formula of each of surfactants listed in Table 2 is shown below.

Accurate quantitative measurement of an analyte in a test sample containing blood platelet can be achieved by using the blood analysis method, dry analytical element or analytical kit according to the invention irrespective of mode of processing of a test sample.

The invention claimed is:

1. A dry analytical element comprising a support, at least one reaction layer containing a color indicator and at least one spreading layer containing a substrate provided on said support in this order, said spreading layer further containing at least one surfactant selected from surfactants that substantially do not destroy blood platelet, said surfactant being selected from the group consisting of silicon series surfactants, wherein said silicon series surfactant is at least one selected from compounds shown by following general formulae (1) to (4):

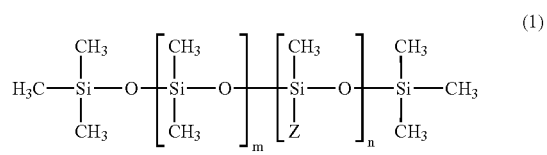

(1)

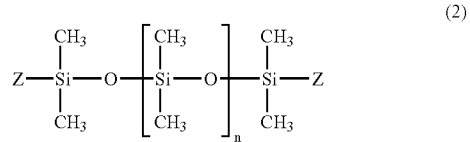

(2)

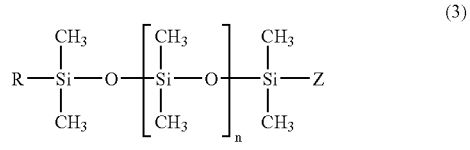

(3)

-continued

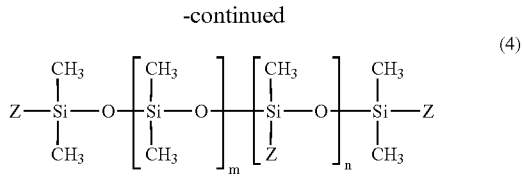

(4)

in which Z represents an organic group represented by the general formula $-R-(C_2H_4O)_a-(C_3H_6O)_b R$.

* * * * *